United States Patent
Spange et al.

(10) Patent No.: US 6,833,394 B2
(45) Date of Patent: Dec. 21, 2004

(54) POLYMERIZABLE DENTAL MATERIAL BASED ON CHROMOPHORIC XEROGELS

(75) Inventors: Stefan Spange, Orlamünde (DE); Norbert Moszner, Eschen (DE); Volker Rheinberger, Vaduz (LI); Peter Burtscher, Nütziders (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 10/209,590

(22) Filed: Jul. 30, 2002

(65) Prior Publication Data

US 2003/0060536 A1 Mar. 27, 2003

(30) Foreign Application Priority Data

Jul. 31, 2001 (DE) .......................... 101 37 372

(51) Int. Cl.$^7$ .............................................. A61K 6/08
(52) U.S. Cl. ..................................................... 523/116
(58) Field of Search ........................................ 523/116

(56) References Cited

U.S. PATENT DOCUMENTS 5,883,153 A * 3/1999 Roberts et al. ............. 523/116

FOREIGN PATENT DOCUMENTS

| DE | 690 18 289 T2 | 1/1990 |
|---|---|---|
| DE | 40 02 726 A1 | 9/1990 |
| DE | 198 11 900 A1 | 9/1999 |
| DE | 198 46 660 A1 | 4/2000 |
| DE | 199 50 284 A1 | 4/2001 |
| EP | 0 744 172 A2 | 11/1996 |
| EP | 0 948 955 A1 | 10/1999 |
| WO | WO 93/00878 | 1/1993 |

OTHER PUBLICATIONS

Roempp Chemielexikon "Chromophore" (2002).
Claude et al., "Organically Modified Silicates that Exhibit Non–Linear Optical Properties by the Sol–Gel Technique." *Polymer Reprints (American Chemical Society, Division of Polymer Chemistry )*, Bd. 34, XP 008010318 p. 709 (1993).

* cited by examiner

Primary Examiner—Kriellion A. Sanders
(74) Attorney, Agent, or Firm—Nixon Peabody LLP

(57) ABSTRACT

Dental materials based on polymerizable binders, which contain at least one chromophoric xerogel of the formula I:

$$(SiO_2)_a(SiO_{1.5}\text{-Sp-X-CG})(Me_nO_m)_b \qquad (I)$$

Figure 1:
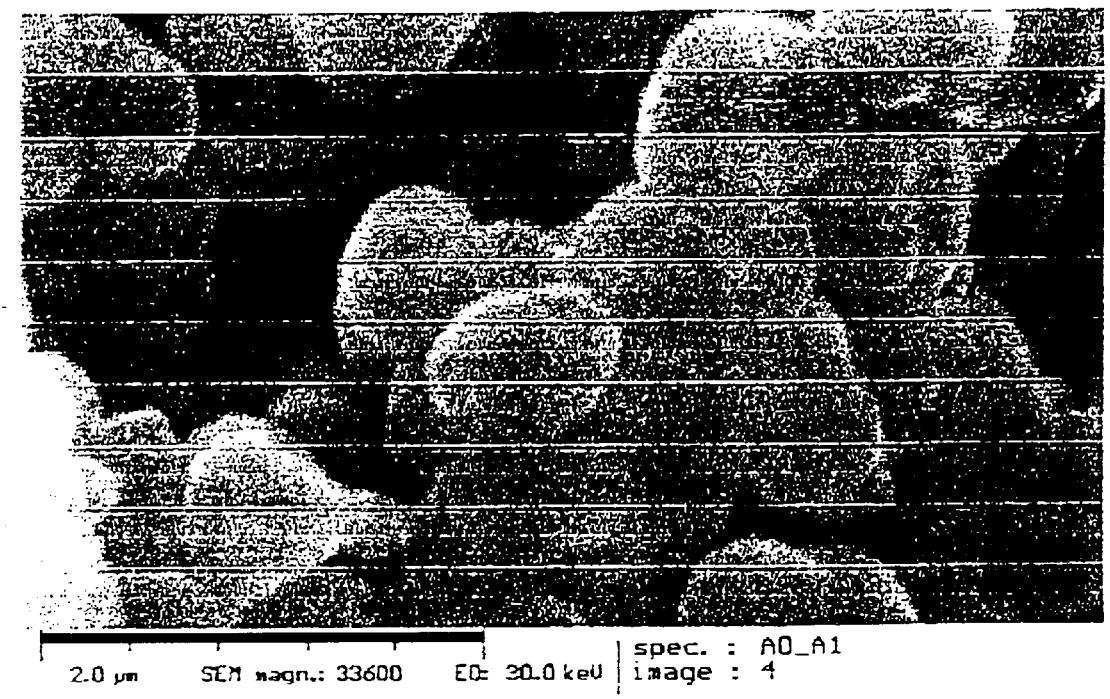

in which Me represents a main-group metal of the $2^{nd}$ to $3^{rd}$ main groups or a transition metal of the $4^{th}$ sub-group of the periodic table of elements; n being equal to 1 or 2, m being equal to 1 or 2 if n is equal to 1 and m being equal to 3 if n is equal to 2; Sp is a $C_1$ to $C_{10}$ alkylene radical or $C_2$ to $C_{10}$ oxyalkylene radical with 1 to 4 oxygen atoms or is absent; X is a compound group, such as CO—O, O—CO, CO—NH, NH—CO, O—CO—NH, NH—CO—O, NR, O or S or is absent, R being hydrogen or a $C_1$ to $C_5$ alkyl radical; CG is a chromophore; a is an integer from 0 to 20 and b is an integer from 0 to 5.

20 Claims, 2 Drawing Sheets

Electron microscope photograph of the chromophoric xerogel from Example 1

POLYMERIZABLE DENTAL MATERIAL BASED ON CHROMOPHORIC XEROGELS

The invention relates to dental materials which contain chromophoric xerogels as colouring component.

Dental materials are mostly reacted with coloured substances for aesthetic reasons in order to match them optically to the natural tooth substance. To this end, dyes or pigments are used as a rule. In the case of photopolymerizable dental materials the problem arises that both dyes and pigments adversely affect the full-curing depth, i.e. lead to a reduction in the full-curing depth. This effect occurs more markedly with filling composites in which the addition of fillers also leads to an additional reduction in the transparency of the material. Accordingly, a full-curing depth of at least 1.5 mm is required for restorative materials according to the international standard ISO 4049 (2000).

For colouring agents used in dental materials there is a range of basic requirements (cf. L. -A. Linden, Photocuring of polymeric dental materials and plastic composite resins", in: Radiation curing in polymer science and technology, Vol. IV., Pub. J. P. Fouassier und J. F. Rabek, Elsevier Appl. Sci., London and New York 1993, 402 ff.), in particular colour stability over many years, stability vis-à-vis heat, for example during the consumption of hot food and chemical stability vis-à-vis oxidants or reduction agents. Furthermore dental colouring agents must not dissolve in fat or water, alcohol or other solvents, have to behave inertly vis-à-vis the other components of dental materials and must be toxicologically acceptable. For these reasons pigments are predominantly used. The pigments can generally be divided into inorganic and organic pigments. Inorganic pigments are often metal oxides or hydroxides, such as e.g. titanium dioxide or ZnO as white pigment, ferric oxide ($Fe_2O_3$) as red pigment or ferric hydroxide (FeOOH) as yellow pigment. The organic pigments can be divided inter alia into azo pigments (e.g. monoazo yellow and orange pigments, disazo pigments or α-naphthol pigments) and non-azo or polycyclic pigments (e.g. phthalocyanine, quinacridon, perylene or flavanthrone pigments) (cf W. Herbst und K. Hunger, Industrielle organische Pigmente, VCH, Weinheim 1987, 4 ff).

The object of the invention is to prepare coloured dental materials with an improved full-curing depth during photopolymerization.

This object is achieved by dental materials which contain as colouring pigment a chromophoric xerogel of formula I:

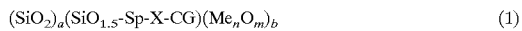

(1)

in which:

Me represents a main-group metal of the $2^{nd}$ to $3^{rd}$ main groups or a transition metal of the $4^{th}$ sub-group of the periodic table of elements;

n is 1 or 2, m being equal to 1 or 2 if n is equal to 1 and m being equal to 3 if n is equal to 2;

Sp is a $C_1$ to $C_{10}$ alkylene radical or $C_2$ to $C_{10}$ oxyalkylene radical with 1 to 4 oxygen atoms or is absent;

X is a compound group, such as CO—O, O—CO, CO—NH, NH—CO, O—CO—NH, NH—CO—O, NR, O or S or is absent, R being hydrogen or a $C_1$ to $C_6$ alkyl radical;

CG is a chromophore;

a is an integer from 0 to 20 and b is an integer from 0 to 5.

X and Sp are preferably not absent at the same time.
Preferred meanings for the stated variables are:

Me Ti, Zr and/or Al;

Sp a $C_1$ to $C_4$ alkylene radical, preferably a propylene radical;

X CO—NH, NH—CO, O—CO—NH, NH—CO—O or NR;

R hydrogen or a $C_1$ to $C_4$ alkyl radical, preferably methyl;

CG a 4-nitrophenyl group, aromatic azo group, di- or triarylmethane group, xanthene group or anthraquinione group;

a 0,1,2,3,4 or 5; and/or b 0,1,2 or 3.

By aromatic azo groups are meant groups with the general structure $R^1$—N═N—$R^2$, $R^1$ and $R^2$ representing aromatic radicals.

The preferred meanings can be chosen independently of each other. Particularly preferred however are naturally xerogels in which several or all variables have one of the preferred meanings.

Xerogels are solids which form from silica gels if the liquid dispersion agent is removed by evaporation, suction or pressing. They are colloidal, tight or loose, shaped or unshaped silicic acid which has a fine pore structure and thus a high adsorption capacity (cf. Ullmanns Encyklopädie der technischen Chemie, $4^{th}$ Edition, Vol. 21, Verlag Chemie, Weinheim etc., 1982, 458 ff). Silica gels of very variable structure are accessible by the sol-gel processing of mixtures of silicic acid esters, e.g. of a tetraalkoxysilane with an organically modified trialkoxysilane, or with other metal alkoxides, such as e.g. aluminium, titanium or zirconium alkoxides (cf. C. J. Brinker and G. W. Scherer, Sol-Gel Science, Academic Press, Bostin etc. 1990, 2 ff). During the hydrolytic condensation of such mixtures in solution a Sol-phase primarily forms, which changes into a gel which consists of an inorganic heteropolysiloxane network and the solvent physically incorporated into it. By evaporating off the solvent the correspondingly compressed dry xerogel is finally obtained. According to the invention by xerogels are preferably meant xerogels in the narrower sense, i.e. xerogels which, during drying, suffer a volume contraction relative to the hydrogel.

The chromophoric xerogels according to the invention are accessible via the Sol-Gel process by hydrolytic co-condensation of tetraalkoxysilanes, e.g. tetraethoxysilane (TEOS), with chromophoric trialkoxysilanes and optionally further metal alkoxides. By chromophoric trialkoxy silanes are meant silanes which carry a chromophore as organic radical. A coloured xerogel is obtained which is called chromophoric xerogel.

Preferred further metal alkoxides are zirconium and titanium compounds, such as $Zr(OC_2H_5)_4$, $Zr(OC_3H_7)_4$, $Zr(OC_4H_9)_4$, $Ti(OC_2H_5)_4$, $Ti(OC_3H_7)_4$ and $Ti(OC_4H_9)_4$. Preferred aluminium compounds are $Al(OCH_3)_3$, $Al(OC_2H_5)_3$, $Al(OC_3H_7)_3$ and $Al(OC_4H_9)_3$. The metal alkoxides are converted into the corresponding metal oxides $Me_nO_m$ during hydrolytic condensation. $TiO_2$ (Me=Ti), $ZrO_2$ (Me=Zr) or $Al_2O_3$ (Me=Al) are particularly suitable for the modification of silica gels.

Chromophoric trialkoxysilanes are accessible for example by the chemical reaction of propyltrialkoxysilanes functionalized in 3-position, e.g. 3-amino, 3-chloro, 3-isocyanato- or 3-mercaptotriethoxysilane, with suitably functionalized chromophoric compounds, e.g.:

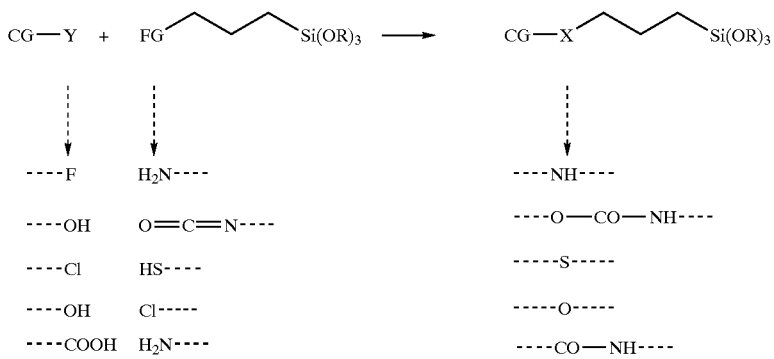

Y and FG each stand for the functional groups with which the chromophoric compound or the alkyltrialkoxysilane has to be equipped in order to facilitate a reaction in the described way while the group X develops. Y and FG preferably have the meaning given above and are preferably also reacted together in the shown combinations.

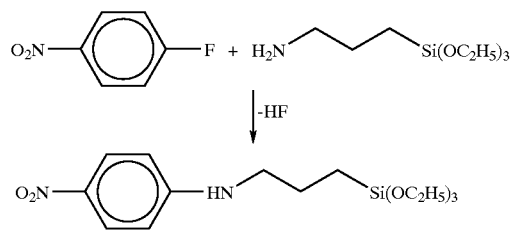

During the preparation of the chromophoric xerogels by hydrolytic condensation, a preferable procedure is to react the hydrolysing silanes in the presence of a hydrolysis and condensation catalyst with the necessary amount of water and stir the resulting mixture. A mixture of TEOS and chromophoric silane is preferably used. The silanes can be present either as such or dissolved in a suitable solvent. Water is added at room temperature or with slight cooling. After the gel has formed the reaction mixture is left to stand for an extended period of time until the reaction is complete and the solvent used is then separated off by heating or evacuation. Considered as solvent are primarily aliphatic alcohols, such as e.g. ethanol or i-propanol, dialkylketones, such as acetone or methyl isobutyl ketone, ethers, such as e.g. diethylethers or tetrahydrofuran (THF), esters, such as ethyl or butyl acetate, and their mixtures. The obtained xerogels can be washed once again with an inert solvent to separate off non-reacted components and then dried until their weight is constant. If the hydrolytic condensation is carried out in the presence of reactive Zr, Ti or Al compounds, then the addition of water should be carried out stepwise at approx. 0 to 30° C. It is preferred to add the water not as such but in the form of water-containing solvents, such as e.g. aqueous ethanol, or to release it by a chemical reaction, for example by esterification.

The synthesis of the chromophoric silane and the hydrolytic condensation are particularly preferably carried out in a one-pot process. This is possible for example if TEOS can be used as solvent during the synthesis of the chromophoric silane and hydrogen fluoride is simultaneously released which acts as a catalyst during the hydrolytic condensation. After the preparation of the silane only water need to be added to form a gel.

Xerogels with a specific BET surface of 50 to 800 m$^2$/g, in particular 200 to 600 m$^2$/g, are preferred. The primary particle size, determined by means of a scanning electron microscope (SEM) of the xerogels, is preferably in the range from 0.1 to 20 $\mu$m, in particular 0.1 to 5 $\mu$m. The particle size is a numerical average. The pore size determined by the BJH method (Barnett E. T. et al., J.Amer.Soc. 73 (1951) 373) is preferably in the range from 1 to 15 nm, in particular 1 to 10 nm. The residual water or solvent content should be below 2.0 wt.-%, preferably below 1.0 wt.-%.

By chromophore, chromophoric group or chromophoric system are meant the colouring radicals which cause a light absorption in the visible region of the spectrum, and not just individual atom groups with $\pi$-electrons (C=C, C=O, C=S, N=O, C=N), the absorption spectrum of which often lies in the ultra violet region of the spectrum (M. Klessinger, Chemie in unserer Zeit, 12 (1978), 1–10).

Single chromophoric groups are preferably used as chromophore, e.g. 4-nitrophenyl derivatives, or also groups which are derived from the known dye classes, such as e.g. azo dyes, di- and triarylmethane dyes, xanthene dyes or anthraquinone dyes, and which do not adversely effect the radical polymerization.

The attachment of the chromophore to the heteropolysiloxane framework preferably takes place via a spacer Sp, the propylene groups being particularly preferred as spacer. Propyltrialkoxysilanes functionalized in 3-position which serve as starting component for the spacer are commercially available.

CO—NH, NH—CO, O—CO—NH, NH—CO—O and NR (with R=H or CH$_3$) are particularly suitable as compound group X. The compound group serves primarily to attach the chromophoric group to the spacer Sp and thus also to the hydrolytically condensable trialkoxysilyl group.

The chromophoric xerogels are characterized by a high colour stability over many years, stability vis-à-vis heat, which is important e.g. when consuming hot food, and chemical vis-à-vis stability against oxidants or reduction agents. Furthermore they are not soluble in fat, water, alcohol or other solvents and behave inertly vis-à-vis the other components of dental materials. In addition they are toxicologically acceptable.

For the preparation of the dental materials according to the invention the chromophoric xerogel is mixed with a polymerizable binder, preferably an organic polymerizable binder. As a rule a dispersion of the xerogel in the binder is obtained. The mixture is then reacted with an initiator for the radical polymerization, preferably a photoinitiator, and optionally reacted with further additives and fillers.

Small amounts of chromophoric xerogels are already sufficient to colour the dental materials, so that they are preferably used in an amount of 0.0001 to 1.0 wt.-%, particularly preferably 0.001 to 0.1 wt.-%, relative to the total mass of the dental material Particularly suitable as radically polymerizable binders are polymerizable monomers, such as mono(meth)acrylates, e.g. methyl, ethyl, butyl, benzyl, furfuryl or phenyl (meth) acrylate, as well as the multifunctional acrylates and methacrylates known as cross-linking monomers, for example dimethacrylates, such as urethane dimethacrylates, bisphenol-A-di(meth)acrylate, bis-GMA (an addition product of methacrylic acid and bisphenol-A-diglycidylether), UDMA (an addition product of 2-hydroxyethyl hydroxyethyl methacrylate and 2,2,4-trimethylhexamethylene diisocyanate), di-, tri- or tetraethylene glycol di(meth) acrylate, decanediol di(meth)acrylate, trimethylolpropane tri(meth)acrylate, pentaerythritol tetra(meth)acrylate, as well as butanediol di(meth)acrylate, 1,10-decanediol di(meth)acrylate or 1,12 dodecanediol di(meth)acrylate as well as mixtures of these monomers.

The binder content is preferably in the range from 10 to 90 wt.-%, particularly preferably 10 to 80 wt.-%, relative to the total mass of the dental material.

In order to initiate the radical photopolymerization, benzophenone, benzoin as well as their derivatives or α-diketones or their derivatives, such as 9,10-penanthrenequinone, diacetyl or 4,4-dichlorobenzil are preferably used. Camphorquinone and 2,2-methoxy-2-phenyl-acetophenone and particularly preferably α-diketones, such as camphorquinone, in combination with amines as reduction agents, preferably tertiary amines, such as e.g. 4-(N,N-dimethylamino)-benzoic acid ester, N,N-dimethylaminoethyl methacrylate, N,N-dimethyl-sym.-xylidine triethanolamine are preferably used. Moreover, acylphosphines, such as e.g. 2,4,6-trimethylbenzoyldiphenyl or bis(2,6-dicholorobenzoyl)-4-N-propylphenlphosphinic oxide are also particularly suitable.

Initiators are preferably used in an amount of 0.1 to 5.0 wt.-% particularly preferably 0.2 to 2.0 wt.-%, in each case relative to the total mass of the dental material.

Furthermore the dental materials according to the invention can be filled with organic or inorganic particles or fibres, to improve the mechanical properties. Preferred inorganic particulate fillers are amorphous spherical materials based on oxides, such as $ZrO_2$ and $TiO_2$, or mixed oxides of $SiO_2$, $ZrO_2$ and/or TiO2, metal oxides with a primary particle size of approx. 40 to 300 nm, splitter polymerisates with a particle size of 10–100 µm (cf. R. Janda, Kunststoffverbundsysteme, VCH Verlagsgesellschaft, Weinheim, 1990, page 225 ff), nanoparticulate or microfine fillers, such as pyrogenic silicic acid or precipitated silicic acid, as well as macro- or minifillers, such as quartz, glass ceramic or glass powders with an average particle size of 0.01 to 5 µm as well as X-ray-opaque fillers, such as ytterbium trifluoride and ground X-ray-opaque glasses with an average particle size between approx. 0.5 to 5 µm. Moreover, glass fibres, polyamide or carbon fibres can also be used.

The filler content depends on the desired use of the dental material. Cements preferably contain 5 to 60 wt.-%, in particular 20 to 60 wt.-% facing materials preferably 50 to 90 wt.-%, in particular 60 to 80 wt.-%, and filling composites preferably 50 to 90 wt.-%, in particular 75 to 85 wt.-% filler, in each case relative to the total mass of the dental material.

The compositions used according to the invention can optionally contain further additives, such as e.g. stabilizers, aromatics, microbicidal active ingredients, optical whiteners, plasticizers or UV absorbers, inhibitors to prevent a premature polymerization and photostabilizers for protection against photooxidative degradation. These additives are preferably used in small amounts of in total 0.1 to 3.0, in particular 0.1 to 1.0 wt.-%, relative to the total mass of the dental material.

During polymerization, the dental materials according to the invention surprisingly show a greater full-curing depth compared with materials with conventional pigments. In addition the chromophoric xerogel content can be clearly reduced compared with conventional pigments, without a reduction in the colour intensity occurring.

Dental materials are preferred which contain
(a) 0.0001 to 1.0 wt.-%, in particular 0.001 to 0.1 wt.-% chromophoric xerogel of the general formula (I),
(b) 10 to 98 wt.-%, in particular 10 to 80 wt.-% polymerizable binder,
(c) 0.1 to 5.0 wt.-%, in particular 0.2 to 2.0 wt.-% polymerization initiator and
(d) 0 to 90 wt.-%, in particular 0 to 80 wt.-% fillers,
in each case relative to the total mass of the dental material.

The dental materials are particularly suitable as cements, facing materials and in particular filling composites.

A particularly preferred cement contains:
(a) 0.0001 to 1.0 wt.-%, in particular 0.001 to 0.1 wt.-% chromophoric xerogel of the general formula (I),
(b) 10 to 90 wt. %, in particular 20 to 50 wt.-% polymerizable binder,
(c) 0.1 to 5.0 wt.-%, in particular 0.2 to 2.0 wt.-% polymerization initiator and
(d) 5 to 60 wt.-%, in particular 20 to 60 wt.-% fillers,
in each case relative to the total mass of the cement.

A particularly preferred facing material contains:
(a) 0.0001 to 1.0 wt.-%, in particular 0.001 to 0.1 wt.-% chromophoric xerogel of the general formula (I),
(b) 10 to 50 wt.-%, in particular 10 to 30 wt.-% polymerizable binder,
(c) 0.1 to 5.0 wt.-%, in particular 0.2 to 2.0 wt.-% polymerization initiator and
(d) 50 to 90 wt.-%, in particular 60 to 80 wt.-% fillers,
in each case relative to the total mass of the facing material.

A particularly preferred filling composite contains:
(a) 0.0001 to 1.0 wt.-%, in particular 0.001 to 0.1 wt.-% chromophoric xerogel of the general formula (I),
(b) 10 to 50 wt.-%, in particular 15 to 25 wt.-%. polymerizable binder,
(c) 0.1 to 5.0 wt.-%., in particular 0.2 to 2.0 wt.-% polymerization initiator and
(d) 50 to 90 wt.-%, in particular 75 to 85 wt.-% fillers,
in each case relative to the total mass of the composite.

The invention is explained in more detail in the following with the help of examples.

EXAMPLES

Example 1

Synthesis of a Chromophoric Xerogel 3.527 g 4-fluoronitrobenzol (0.025 mol), 25.88 ml tetraethoxysilane (26.041 g, 0.116 mol) and 11.03 ml 3-aminopropyltrimethoxysilane (11.2056 g, 0.0625 mol) were mixed by stirring in a three-necked flask. A bright-yellow, slightly cloudy solution formed. This was boiled at 130° C. for 5 hours. The reaction mixture became clear and darker. The mixture was slowly cooled down and left to stand overnight. 50 ml of ethanol was then added, whereupon a slight clouding could be ascertained 3 ml water was then added dropwise. Heating then took place and the mixture became thicker and cloudier. A further 100 ml water was added and the suspension was then stirred for 2 hours and then filtered off. It was washed with water and ethanol and dried in an desiccator over calcium chloride (vacuum) until its weight was constant. An overall yield of approx. 90% resulted.

Figure 2:
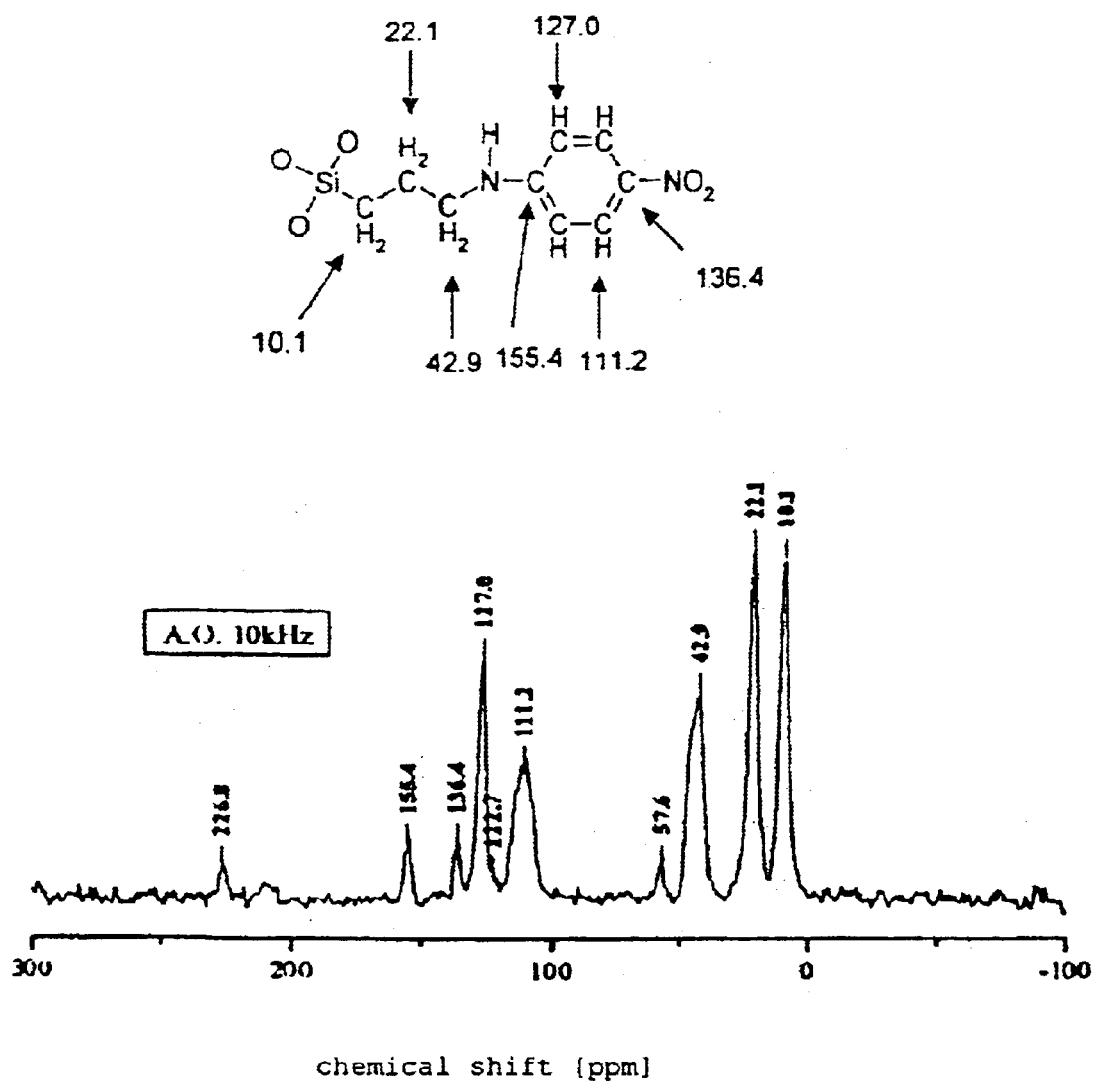

The chromophoric xerogel was examined using an electron microscope and $^{13}$C-MAS-CP-solids NMR. An electron microscope photograph of the product is shown in FIG. 1. The NMR examination had the results shown in FIG. 2.

Example 2

Preparation of a Yellow-Coloured Dental Composite Based on a Chromophoric Xerogel In order to dye composites the colour of teeth, yellow pigments based on ferric oxide (light yellow 8G) are used above all. Accordingly a thus-coloured composite was selected as comparison example. It was established in a preliminary test, which concentration of chromophoric xerogel is necessary in order to obtain the same colour effect as with light yellow 8G.

Composition of the Composite Pastes (Amounts in wt.-%) and Their Full-Curing Depth During the Photopolymerization

|  | Comparison paste | Xerogel paste |
|---|---|---|
| Monomer | 21.8 | 21.8 |
| Filler | 77.9 | 78.19 |
| Light yellow 8G | 0.3 | 0 |
| Xerogel from Ex. 1 | 0 | 0.01 |
| Full-curing depth (mm) | 3.9 | 4.9 |

The method for determining the full-curing depth involved the procedure according to ISO-4049. A cylindrical opening in a steel mould (h=6 mm, d=4 mm) was filled with the composite paste and polymerized for 40 s with a polymerization device. The composite was then removed from the metal mould and the non-polymerized proportion is scratched off from the cured part with a plastic spatula. The thickness of the cured composite was then determined with a slide gauge. The polymerization lamp Astralis 5 (Vivadent) was used for the examinations.

The tests showed that, with a concentration of 0.01% chromophoric xerogel, the same colour effect is achieved, as with 0.3% light yellow 8G. A clearly higher full-curing depth (+25%) was achieved.

Example 3

Preparation of a Dark-Coloured Dental Composite Based on a Chromophoric Xerogel In tooth-coloured composites red, brown and black pigments are also used along with yellow pigments, in order to obtain an optimum tooth colour. A composite was prepared in the Vita Colour A3.5, a relatively dark colour, the yellow pigments light yellow 8 G and the chromophoric xerogel again being compared.

Composition of the Composite Pastes (Amounts in wt.-%) and their Full-Curing Depth During the Photopolymerization

|  | Comparison paste | Xerogel paste |
|---|---|---|
| Monomer and filler | 99.9347 | 99.9582 |
| Brown pigment | 0.0301 | 0.0301 |
| Red pigment | 0.0103 | 0.0103 |
| Black pigment | 0.0004 | 0.0004 |
| Light yellow 8 G | 0.0245 | 0 |
| Xerogel from Ex. 1 | 0 | 0.0010 |
| Full-curing depth (mm) | 3.6 | 4.0 |

The positive effect of the chromophoric xerogels was demonstrated also with this very dark composite. With the same colour, an improvement of 0.4 mm in the full-curing depth is achieved, which represents a significant difference for dark colours.

What is claimed is:

1. A dental material comprising a polymerizable binder and at least one chromophoric xerogel of the formula (I):

$$(SiO_2)_a(SiO_{1.5}\text{-Sp-X-CG})(Me_nO_m)_b \qquad (I)$$

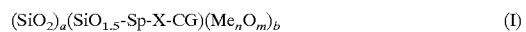

in which

Me represents a main-group metal of the 2nd to 3rd main groups or a transition metal of the 4th sub-group of the periodic table of the elements;

n is 1 or 2, m being equal to 1 or 2 if n is equal to 1 and m being equal to 3 if n is equal to 2;

Sp is a $C_1$ to $C_{10}$ alkylene radical or $C_2$ to $C_{10}$ oxyalkylene radical with 1 to 4 oxygen atoms or is absent;

X is a compound group CO—O, O—CO, CO—NH, NH—CO, O—CO—NH, NH—CO—O, NR, O or S or is absent, R being hydrogen or a $C_1$ to $C_6$ alkyl radical;

CG is a chromophore;

a is an integer from 0 to 20 and b is an integer from 0 to 5.

2. The dental material according to claim 1, wherein

Me is Ti, Zr or Al; and/or

Sp is a $C_1$ to $C_4$ alkylene radical;

X is CO—NH, NH—CO, O—CO—NH, NH—CO—O or NR;

R is hydrogen or a $C_1$ to $C_4$ alkyl radical; and/or

CG is a 4-nitrophenyl group, aromatic azo group, di- or triarylmethane group, xanthene group or anthraquinione group; and/or a is 0, 1, 2, 3, 4 or 5; and/or b is 0, 1, 2 or 3.

3. The dental material according to claim 1, further comprising an initiator for the radical polymerization.

4. The dental material according to claim 3, wherein said initiator is a benzophenone, benzoin, α-diketone, acylphosphine or a derivative thereof.

5. The dental material according to claim 3, further comprising an amine as reduction agent.

6. The dental material according to claim 1, wherein said polymerizable binder is a mono(meth)acrylate, multifunctional (meth)acrylate, or a mixture thereof.

7. The dental material according to claim 1, further comprising inorganic, organic, particulate or fibrous filler.

8. The dental material according to claim 3, containing (a) 0.0001 to 1.0 wt.-% chromophoric xerogel of the general formula (I);

(b) 10 to 98 wt.-% polymerizable binder; and
(c) 0.1 to 5.0 wt.-% polymerization initiator,
in each case relative to the total mass of the dental material.

9. The dental material according to claim 8, further comprising (d) 0 to 90 wt.-/%, relative to the total mass of the dental material.

10. A chromophoric xerogel of formula I:

$$(SiO_2)_a(SiO_{1.5}\text{-Sp-X-CG})(Me_nO_m)_b \quad (I)$$

in which:
- Me represents a main-group metal of the 2nd to 3rd main groups or a transition metal of the 4th sub-group of the periodic table of elements;
- n is 1 or 2, m being equal to 1 or 2 if n is equal to 1 and m being equal to 3 if n is equal to 2;
- Sp is a $C_1$ to $C_{10}$ alkylene radical or $C_2$ to $C_{10}$ oxyalkylene radical with 1 to 4 oxygen atoms or is absent;
- X is a compound group CO—O, O—CO, CO—NH, NH—CO, O—CO—NH, NH—CO—O, NR, O or S or is absent, R being hydrogen or a $C_1$ to $C_6$ alkyl radical;
- CG is a chromophore;
- a is an integer from 0 to 20 and
- b is an integer from 0 to 5.

11. A method for the preparation of a dental material comprising using the chromophoric xerogel according to claim 10.

12. The method according to claim 11, wherein said dental material is a photo-curable dental material.

13. The method according to claim 11, wherein said dental material comprises cements, facing materials or filling composites.

14. A process for the preparation of a chromophoric xerogel according to claim 10, in which a tetraalkoxysilane and a chromophoric trialkoxysilane are reacted together by hydrolytic condensation.

15. The process according to claim 14, in which the hydrolytic condensation is carried out in the presence of one or more, further metal alkoxides.

16. The dental material according to claim 4, wherein said initiator is 9,10-penanthrenequinone, diacetyl, 4,4-dichlorobenzil, camphorquinone, 2,2-methoxy-2-phenyl-acetophenone, 2,4,6-trimethylbenzoyldiphenyl or bis(2,6-dicholorobenzoyl)-4-N-propylphenylphosphinic oxide, or a derivative thereof.

17. The dental material according to claim 5, wherein said amine is 4-(N,N-dimethylamino)-benzoic acid ester, N,N-dimethylaminoethyl methacrylate, N,N-dimethyl-sym.-xylidine and/or triethanolamine.

18. The dental material according to claim 6, wherein said polymerizable binder is a methyl, ethyl, butyl, benzyl, furfuryl or phenyl (meth)acrylate, bisphenol-A-di(meth)acrylate, bis-GMA (an addition product of methacrylic acid and bisphenol-A-diglycidylether), UDMA (an addition product of 2-hydroxyethyl methacrylate and 2,2,4-trimethylhexamethylene diisocyanate), di-, tri- or tetraethylene glycol di(meth)acrylate, decanediol di(meth)acrylate, trimethylolpropane tri(meth)acrylate, pentaerythritol tetra(meth)acrylate, butanediol di(meth)acrylate, 1,10-decanediol di(meth)acrylate or 1,12 dodecanediol di(meth)acrylate or a mixture thereof.

19. The dental material according to claim 8, containing
(a) 0.001 to 0.1 wt.-% chromophoric xerogel of the general formula (I);
(b) 10 to 80 wt.-% polymerizable binder; and
(c) 0.2 to 2.0 wt.-% polymerization initiator,
in each case relative to the total mass of the dental material.

20. The dental material according to claim 9, containing (d) 0 to 80 wt.-% filler, relative to the total mass of the dental material.

* * * * *